(12) United States Patent
Sprenger et al.

(10) Patent No.: US 9,161,563 B2
(45) Date of Patent: Oct. 20, 2015

(54) OLIGOSACCHARIDE MIXTURE AND FOOD PRODUCT COMPRISING THIS MIXTURE, ESPECIALLY INFANT FORMULA

(75) Inventors: Norbert Sprenger, Savigny (CH); Jean-Richard Neeser, Savigny (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/988,967

(22) PCT Filed: Nov. 21, 2011

(86) PCT No.: PCT/EP2011/070565
§ 371 (c)(1),
(2), (4) Date: May 22, 2013

(87) PCT Pub. No.: WO2012/069415
PCT Pub. Date: May 31, 2012

(65) Prior Publication Data
US 2013/0236423 A1    Sep. 12, 2013

(30) Foreign Application Priority Data

Nov. 23, 2010 (EP) .................................... 10192232

(51) Int. Cl.
| A01N 63/00 | (2006.01) |
| A23L 1/29 | (2006.01) |
| A23L 1/308 | (2006.01) |
| A61K 31/702 | (2006.01) |
| A61K 45/06 | (2006.01) |
| C07H 3/04 | (2006.01) |
| C07H 3/06 | (2006.01) |
| C07H 13/04 | (2006.01) |
| A61K 31/716 | (2006.01) |
| A61K 35/741 | (2015.01) |

(52) U.S. Cl.
CPC ................ *A23L 1/296* (2013.01); *A23L 1/308* (2013.01); *A61K 31/702* (2013.01); *A61K 31/716* (2013.01); *A61K 35/741* (2013.01); *A61K 45/06* (2013.01); *C07H 3/04* (2013.01); *C07H 3/06* (2013.01); *C07H 13/04* (2013.01); *A23V 2002/00* (2013.01)

(58) Field of Classification Search
CPC ........................................................ A01N 63/00
USPC ................................................ 424/93.4, 93.1
See application file for complete search history.

(56) References Cited

U.S. PATENT DOCUMENTS

| 2003/0129278 A1 | 7/2003 | Stahl et al. |
| 2003/0181401 A1 | 9/2003 | Takada et al. |
| 2007/0275881 A1 | 11/2007 | Morrow et al. |
| 2009/0041736 A1* | 2/2009 | Sprenger et al. ........... 424/93.45 |
| 2009/0117256 A1 | 5/2009 | Khatib et al. |

FOREIGN PATENT DOCUMENTS

| EP | 2072052 | 6/2009 |
| EP | 2143341 | 1/2010 |
| WO | 2005067962 | 7/2005 |
| WO | 2006087391 | 8/2006 |
| WO | 2007090894 | 8/2007 |
| WO | 2007114683 | 10/2007 |
| WO | 2008116916 | 10/2008 |
| WO | 2010003803 | 1/2010 |

OTHER PUBLICATIONS

Thurl et al. "Variations of Neutral Oligosaccharides and Lactose in Human Milk During the Feeding" Zeitschrift Fuer Ernaehrungswissenschaft, vol. 32, pp. 262-269—XP002071967.
Russian Office Action for Application No. 2013128575/13(042575), dated Mar. 30, 2015, 11 pages.

* cited by examiner

*Primary Examiner* — Karen Cochrane Carlson
*Assistant Examiner* — Natalie Moss
(74) *Attorney, Agent, or Firm* — K&L Gates LLP

(57) ABSTRACT

The invention discloses an oligosaccharide mixture comprising 5-70 wt % of at least one N-acetylated oligosaccharide, 5-90 wt % of at least one neutral oligosaccharide, 2-50 wt % of at least one sialylated oligosaccharide, and/or 5-70 wt % of at least one fucosylated oligosaccharide. The invention also discloses a food product, especially an infant formula, comprising said oligosaccharide mixture.

15 Claims, No Drawings

OLIGOSACCHARIDE MIXTURE AND FOOD PRODUCT COMPRISING THIS MIXTURE, ESPECIALLY INFANT FORMULA

CROSS REFERENCE TO RELATED APPLICATIONS

The present application is a National Stage of International Application No. PCT/EP2011/070565, filed Nov. 21, 2011, which claims priority to European Patent Application No. 10192232.6, filed Nov. 23, 2010, the entire contents of which are being incorporated herein by reference.

FIELD OF THE INVENTION

The invention relates to an oligosaccharide mixture and to a food product comprising said oligosaccharide mixture, especially infant formula.

BACKGROUND OF THE INVENTION

The human colon is colonised by a wide range of bacteria having both positive and negative effects on the gut's physiology, as well as having other systemic influences. The predominant groups of bacteria found in the colon include *Bacteroides* species, in particular *Bifidobacteria, Eubacteria, Clostridia* and *Lactobacilli*. These bacteria have fluctuating activities in response to substrate availability, redox potential, pH, $O_2$ tension and their distribution in the colon. In general intestinal bacteria can be divided into species exerting either potentially harmful or beneficial effects on their host. Pathogenic effects (which may be caused by *Clostridia* or *Bacteroides*, for example) include diarrhoea, infections, liver damage, carcinogenesis and intestinal putrefaction. Health-promoting effects may be induced through the inhibition of the growth of harmful bacteria, the stimulation of immune functions, improvements in the digestion and absorption of essential nutrients and the synthesis of vitamins. An increase in the numbers and/or activities of bacterial groups (such as *Bifidobacteria* and *Lactobacilli*) that may have health promoting properties is desirable.

Concerning the specific case of infants, immediately before birth, the gastrointestinal tract of an infant is thought to be sterile. During the process of birth, it encounters bacteria from the digestive tract and skin of the mother and starts to become colonised. Large differences exist with respect to the composition of the gut microbiota in response to the infant's feeding. The faecal flora of breast-fed infants includes appreciable populations of bifidobacteria with some *Lactobacillus* species, whereas formula-fed infants have more complex microbiota, with *Bifidobactera* species and *Bacteroides* species, *Clostridia* and *Streptococci* being usually present. After weaning, a pattern of gut microbiota resembling that of an adult pattern becomes established.

Mother's milk is recommended for all infants. However, in some cases breastfeeding is inadequate or unsuccessful for medical reasons or because of mother choice not to breast-feed. Infant formulae have been developed for these situations.

One approach to promote the numbers and/or activities of beneficial bacteria in the colon is the addition of prebiotics to foodstuffs. A prebiotic is a non-digestible food ingredient that beneficially affects the host by selectively stimulating the growth and/or activity of one or a limited number of bacteria in the colon, thereby improving the host's health. Such ingredients are non-digestible in the sense that they are not broken down and absorbed in the stomach or small intestine and thus pass intact to the colon where they are selectively fermented by the beneficial bacteria. Examples of prebiotics include certain oligosaccharides, such as fructooligosaccharides (FOS) and galactooligosaccharides (GOS).

Human milk is known to contain a larger amount of indigestible oligosaccharides than most other animal milks. In fact, indigestible oligosaccharides represent the third largest solid component (after lactose and lipids) in breast milk, occurring at a concentration of 12-15 g/l in colostrum and 5-8 g/l in mature milk. Human milk oligosaccharides are highly resistant to enzymatic hydrolysis, indicating that these oligosaccharides may display essential functions not directly related to their caloric value.

As the understanding of the composition of human milk improves, it has also been proposed to add prebiotics to infant formula. Various infant formulae supplemented with prebiotics such as mixtures of fructooligosacccharides and galactooligosaccharides, for example, are commercially available. However, such mixtures provide only an approximation to the mixture of oligosaccharides present in human milk. Over 100 different oligosaccharide components have been detected in human milk, some of which have not yet been detected, or have been detected only in small quantities, in animal milks such as bovine milk. Some sialylated oligosaccharides and fucosylated oligosaccharides are present both in bovine milk and in colostrum, but only in very small quantities.

EP 0 975 235 B1 from Abbott Laboratories describes a synthetic nutritional composition comprising one or more human milk oligosaccharides, wherein the HMOs in the composition are chosen among a group of eight HMOs (3-fucosyllactose, lacto-N-fucopentaose III, lacto-N-fucopentaose II, difucosyllactose, 2'-fucosyllactose, lacto-N-fucopentaose I, lacto-N-neotetraose and lacto-N-fucopentaose V) wherein said composition is intended for cases of normal, healthy infants, children, adults or subjects having specialized needs such as those that accompany certain pathological conditions. This European patent states that, generally speaking, oligosaccharides protect infants from viral and bacterial infections of the respiratory, gastrointestinal and uro-genital tracts.

An object of the present invention is to provide an oligosaccharide mixture which is effective as a prebiotic, particularly in the human gut.

There is a need for a food product, especially targeted at babies, infants and/or new born infants, that help securing a normal immune or inflammation status or mitigate or reduce the effect of food allergies.

There is a need for a food product that provides the above benefits while preserving a balanced normal metabolism in the individual.

There is a need for an improvement of human gut conditions, by a non-drug-based intervention that is compatible with fragile individuals like infants or babies.

There is a need for a food product that provides an oral tolerance to allergens.

SUMMARY OF THE INVENTION

In one aspect the invention relates to an oligosaccharide mixture which comprises:
  i. 5-70 wt % of at least one N-acetylated oligosaccharide selected from the group comprising N-acetyl-galactosaminyl-lactose (=GalNAcα1,3Galβ1,4Glc=3'GalNAc-lac) and galactosyl-N-acetyl-galactosaminyl-lactose (=Galβ1,6GalNAcα1,3Galβ1,4Glc=6'Gal-3GalNAc-lac), and
  ii. 5-90 wt % of at least one galacto-oligosaccharide selected from the group comprising one or more of the following galactosyl-disaccharides or galactosyl-oligosaccharides: Galβ1,6Gal (=β1,6-digalactoside), Galβ1,6Galβ1,4Glc (=6'Gal-lac), Galβ1,6Galβ1,6Glc, Galβ1,3Galβ1,3Glc, Galβ1,3Galβ1,4Glc (=3'Gal-lac), Galβ1,6Galβ1,6Galβ1,4Glc (=6',6-diGal-lac), Galβ1,6Galβ1,3Galβ1,4Glc (=6',3-diGal-lac) Galβ1,6Galβ1,4Glc (=3',6-diGal-lac), Galβ1,3Galβ1,3Galβ1,4Glc (=3',3-diGal-lac), Galβ1,4Galβ1,4Glc (=4' Gal-lac) and Galβ1,4Galβ1,4Galβ1,4Glc (=4',4-diGal-lac), and iii. 2-50 wt % of at least one sialylated oligosaccharide selected from the group comprising 3'-sialyllactose (NeuAcα2,3Galβ1,4Glc) and 6'-sialyllactose (NeuAcα2,6Galβ1,4Glc), and/or iv. 5-70 wt % of at least one fucosylated oligosaccharide selected from the group comprising Fucα1,2Galβ1,4Glc (2'-fucosyllactose), Galβ1,4(Fucα1,3)Glc (3-fucosyllactose), Fucα1,2Galβ1,4(Fucα1,3)Glc (difucosyllactose), lacto-N-fucopentaoses (that is to say Fucα1,2Galβ1,3GlcNAcβ1,3Galβ1,4Glc -lacto-N-fucopentaose I-, Galβ1,3(Fucα1,4)GlcNAcβ1,3Galβ1,4Glc-lacto-N-fucopentaose II-, Galβ1,4(Fucα1,3)GlcNAcβ1,3Galβ1,4Glc-lacto-N-fucopentaose III-, and Galβ1,3GlcNAcβ1,3Galβ1,4(Fucα1,3)Glc-lacto-N-fucopentaose V-), Fucα1,2Galβ1,3(Fucα1,4)GlcNAcβ1,3Galβ1,4Glc (lacto-N-difucohexaose I), Galb1,4(Fuca1,3)GlcNAcb1,6(Galb1,3GlcNAcb1,3)Galb1,4Glc (monofucosyllacto-N-hexaose), Fucα1,2Galβ1,3 GlcNAcβ1,3(Galb1,4(Fuca1,3)GlcNAcb1,6)Galb1,4Glc (Difucosyllacto-N-hexaose I), and Galβ1,4(Fuca1,3)GlcNAcβ1,3(Galb1,4(Fuca1,3)GlcNAcb1,6)Galb1,4Glc (Difucosyllacto-N-neohexaose II).

The compounds are defined by their structures, where GalNAc is N-acetyl galactosamine, GlcNAc is N-acetyl glucosamine, Gal is galactose, NeuAc is N-acetyl neuraminic acid, Fuc is fuctose and Glc is glucose.

The above mixture of ingredients is a new protective and immuno-modulating composition that is particularly effective as a prebiotic. The mixture is structurally closer to human breast milk oligosaccharides than commercially available prebiotic ingredients, such as FOS and GOS, due to the fact it comprises, for example, a mixture of specific acidic (sialylated) and neutral (fucosylated or N-acetyl-lactosamine or other) oligosaccharides.

In one embodiment the oligosaccharide mixture may be derived from animal milk, such as one or more of cow, goat or buffalo milk.

In another embodiment the oligosaccharide mixture is a synthetic composition.

In another aspect the invention relates to a food product comprising an oligosaccharide mixture as described above. Optionally the food product is proposed as infant food or formula, but the product may be used in any food or drink consumed by babies, infants or adults. Adults usually use the oligosaccharide mixture according to the invention when needed, in particular in the technical field of clinical nutrition. Consumption of a food product containing such an oligosaccharide mixture as a prebiotic will selectively promote the growth and/or activity of one or a limited number of beneficial bacteria in the colon, and will thus improve the host's health.

DETAILED DESCRIPTION OF THE INVENTION

As used herein, the following terms have the following meanings.

The term "infant" means a child under the age of 12 months.

The term "young child" means a child aged between one and three years.

The term "infant formula" means a foodstuff intended for particular nutritional use by infants during the first four to six months of life and satisfying by itself the nutritional requirements of this category of person (Article 1.2 of the European Commission Directive 91/321/EEC of May 14, 1991 on infant formulae and follow-on formulae).

The term "follow-on formula" means a foodstuff intended for particular nutritional use by infants aged over four months and constituting the principal liquid element in the progressively diversified diet of this category of person.

The term "starter infant formula" means a foodstuff intended for particular nutritional use by infants during the first four months of life.

The term "baby food" means a foodstuff intended for particular nutritional use by infants during the first years of life.

The term "infant cereal composition" means a foodstuff intended for particular nutritional use by infants during the first years of life.

The term "growing-up milk" means a milk-based beverage adapted for the specific nutritional needs of young children.

The term "weaning period" means the period during which the mother's milk is substituted by other food in the diet of an infant.

The term "enhancement of the oral tolerance to allergens" means the reduction of the sensibility to allergens when taken orally.

The term "nutritional composition" means a composition which nourishes a subject. This nutritional composition is usually to be taken orally or intraveinously, and it usually includes a lipid or fat source and a protein source.

The term "synthetic composition" means a composition obtained by chemical and/or biological (e.g. enzymes) means, which can be chemically identical to the composition naturally occurring in mammalian milks. A composition is said to be synthetic as soon as at least one of its components is obtained by chemical and/or biological (e.g. enzymes) means.

The term "hypoallergenic composition" means a composition which is unlikely to cause allergic reactions.

The term "N-acetylated" oligosaccharide means an oligosaccharide having an N-acetyl residue.

The term "sialylated oligosaccharide" means an oligosaccharide having a sialic acid residue.

The term "fucosylated oligosaccharide" means an oligosaccharide having a fucose residue.

The term "prebiotic" means non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics. J Nutr.* 1995; 125:1401-12).

The term "probiotic" means microbial cell preparations or components of microbial cells with a beneficial effect on the health or well-being of the host. (Salminen S, Ouwehand A. Benno Y. et al. *"Probiotics: how should they be defined"* Trends Food Sci. Technol. 1999:10 107-10).

An "allergy" is an allergy which has been detected by a medical doctor and which can be treated occasionally or in a more durable manner. A "food allergy" is an allergy with respect to a nutritional product.

All percentages are by weight unless otherwise stated.

The oligosaccharide mixture according to the invention is preferably a hypoallergenic composition.

The invention provides an oligosaccharide mixture which comprises preferably:
i. 5-50 wt % of at least one N-acetylated oligosaccharide selected from the group comprising N-acetyl-galactosaminyl-lactose and galactosyl-N-acetyl-galactosaminyl-lactose,
ii. 5-70 wt % of at least one galacto-oligosaccharide selected from the group comprising one or more of the following galactosyl-disaccharides or galactosyl-oligosaccharides: Galβ1,6Gal, Galβ1,6Galβ1,4Glc, Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc, Galβ1,3Galβ1,3Galβ1,4Glc, Galβ1,4Galβ1,4Glc and Galβ1,4Galβ1,4Galβ1,4Glc,
iii. 2-40 wt % of at least one sialylated oligosaccharide selected from the group comprising 3'-sialyllactose and 6'-sialyllactose, and/or
iv. 10-70 wt % of at least one fucosylated oligosaccharide selected from the group comprising 2'-fucosyllactose, 3-fucosullactose, difucosyllactose, lacto-N-fucopentaoses, lacto-N-difucohexaose I, monofucosyllacto-N-hexaose, Difucosyllacto-N-hexaose I and Difucosyllacto-N-neohexaose II.

More preferably, the mixture comprises:
i. 10-40 wt % of the N-acetylated oligosaccharide,
ii. 5-35 wt % of the galacto-oligosaccharide,
iii. 2-20 wt % of the sialylated oligosaccharide and
iv. 30-60 wt % of the fucosylated oligosaccharide.

A particularly preferred mixture comprises 25 wt % of the N-acetylated oligosaccharide, 20 wt % of the galacto-oligosaccharide, 10 wt % of the sialylated oligosaccharide and 45 wt % of the fucosylated oligosaccharide.

The inventors have discovered that, surprisingly, the oligosaccharide mixture according to the invention, when comprised in a food product, is particularly advantageous for preventing and reducing the risk and/or reducing the severity and/or reducing the occurrence of food allergies and related food allergy effects on health. Said effects are preferably (i) skin effects, atopic dermatitis, rash, or redness; (ii) effects on the immune system or inflammation status ; or (iii) effects on the gastro-intestinal system such as colics, abdominal pain and the like.

The oligosaccharide mixture of the invention may be derived from animal milks. The milk may be obtained from any mammal, in particular from cows, goats, buffalos, horses, elephants, camels or sheep.

Alternatively the oligosaccharide mixture may be prepared by purchasing and mixing the individual components. For example, synthesised galacto-oligosaccharides such as Galβ1,6Gal, Galβ1,6Galβ1,4Glc, Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc, Galβ1,3Galβ1,3Galβ1,4Glc, Galβ1,4Galβ1,4Glc and Galβ1,4Galβ1,4Galβ1,4Glc and mixtures thereof are commercially available under the trademarks Vivinal ® and Elix'or®. Other suppliers of oligosaccharides are Dextra Laboratories, Sigma-Aldrich Chemie GmbH and Kyowa Hakko Kogyo Co., Ltd. Alternatively, specific glycosyltransferases, such as galactosyltransferases may be used to produce galacto-oligosaccharides.

The N-acetylated oligosaccharides may be prepared by the action of glucosaminidase and/or galactosaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced through the use of fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerisation (DP), from DP=1 onwards. Another option is the chemical conversion of keto-hexoses (e.g. fructose) either free or bound to an oligosaccharide (e.g. lactulose) into N-acetylhexosamine or an N-acetylhexosamine containing oligosaccharide as described in Wrodnigg, T. M.; Stutz, A. E. (1999) Angew. Chem. Int. Ed. 38:827-828.

The sialylated oligosaccharides 3'-sialyllactose and 6'-sialyllactose may be isolated by chromatography or filtration from a natural source such as animal milks. Alternatively, they may also be produced by biotechnological means using specific sialyltransferases or sialidases, neuraminidases, either by an enzyme based fermentation technology (recombinant or natural enzymes), by chemical synthesis or by microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards.

The fucosylated oligosaccharide may be selected from the group comprising 2'-fucosyllactose, 3-fucosyllactose, difucosyllactose, lacto-N-fucopentaose I, lacto-N-fucopentaose II, lacto-N-fucopentaose III, lacto-N-fucopentaose V, lacto-N-difucohexaose I, monofucosyllacto-N-hexaose, Difucosyllacto-N-hexaose I and Difucosyllacto-N-neohexaose II.

A particularly preferred fucosylated oligosaccharide is 2'-fucosyllactose.

The fucosylated oligosaccharide may be isolated by chromatography or filtration technology from a natural source such as animal milks. Alternatively, it may be produced by biotechnological means using specific fucosyltransferases and/or fucosidase either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

In a preferred aspect of the invention, the oligosaccharide mixture described above is incorporated into a food product. In the context of the present invention, the term "food product" is intended to encompass any consumable substance. Hence, it may be a product intended for consumption by humans, in particular an infant formula, a follow-up formula, infant or young children food such as infant cereals, and the like. In particular, the oligosaccharide mixtures of the invention can be incorporated into infant formulas, dehydrated milk or cereal mixtures.

Thus the invention also includes a food product comprising the oligosaccharide mixture of the invention. Said food product preferably comprises a protein source, a fat source and a carbohydrate source.

The food product according to the invention also contains a protein source. The type of protein is not believed to be critical to the present invention provided that the minimum requirements for essential amino acid content are met and satisfactory growth is ensured. Thus, protein sources based on whey, casein and mixtures thereof may be used as well as protein sources based on soy. However, the protein source preferably comprises between 20% and 95% of whey proteins and/or proteins derived from whey. As far as whey proteins are concerned, the protein source may be based on acid whey or sweet whey or mixtures thereof and may include alpha-lactalbumin and beta-lactoglobulin in any desired proportions.

The food product according to the present invention generally contains a carbohydrate source. This is particularly preferable in the case where the food product of the invention is an infant formula. In this case, any carbohydrate source conventionally found in infant formulae such as lactose, saccharose, maltodextrin, starch and mixtures thereof may be used although the preferred source of carbohydrates is lactose.

The food product according to the present invention generally contains a source of lipids. This is particularly relevant if the food product of the invention is an infant formula. In this case, the lipid source may be any lipid or fat which is suitable for use in infant formulae. Preferred fat sources include palm oleic, high oleic sunflower oil and high oleic safflower oil. The essential fatty acids linoleic and a-linolenic acid may also be added as may small amounts of oils containing high quantities of preformed arachidonic acid and docosahexaenoic acid such as fish oils or microbial oils. The fat source preferably has a ratio of n-6 to n-3 fatty acids of about 5:1 to about 15:1; for example about 8:1 to about 10:1.

The food product of the invention also contains preferably all vitamins and minerals understood to be essential in the daily diet and in nutritionally significant amounts. Minimum requirements have been established for certain vitamins and minerals. Examples of minerals, vitamins and other nutrients optionally present in the food product of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the food product of the invention may contain emulsifiers and stabilisers such as soy, lecithin, citric acid esters of mono- and di-glycerides, and the like.

The food product of the invention may also contain other substances which may have a beneficial effect such as lactoferrin, nucleotides, nucleosides, and the like.

The food product according to the invention is preferably a synthetic nutritional composition. In this case, it can be a starter infant formula, an infant formula, a baby food, an infant cereal composition, a follow-on formula or a growing-up milk, and said food product is preferably a starter infant formula.

The food product of the invention can further comprise at least one probiotic bacterial strain, said probiotic bacterial strain preferably being *Bifidobacteria* and/or *Lactobacilli*. Said food product is particularly advantageous for the enhancement of the oral tolerance to allergens.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM I-2116, *Lactobacillus reuteri* sold by BioGaia A.B under the trademark Reuteri, *Lactobacillus johnsonii* CNCM I-1225, *Streptococcus salivarius* DSM 13084 sold by BLIS Technologies Limited of New Zealand under the designation K12, *Bifidobacterium lactis* CNCM I-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

In addition to the oligosaccharide mixture of the invention, a food product such as an infant formula may comprise one or more further oligosaccharides which are added separately.

The food product of the invention can further comprise at least one prebiotic, usually in an amount between 0.3 and 10% by weight of food product.

For example the food product can also comprise prebiotics other than the oligosaccharides of the oligosaccharide mixture according to the invention. Prebiotics are usually non-digestible in the sense that they are not broken down and absorbed in the stomach or small intestine and thus remain intact when they pass into the colon where they are selectively fermented by the beneficial bacteria. Examples of prebiotics include certain oligosaccharides, such a fructooligosaccharides (FOS) and galactooligosaccharides (GOS). A combination of prebiotics may be used such as 90% GOS with 10% short chain fructo-oligosaccharides such as in the product by BENEO-Orafti sold under the trademark Orafti® oligofructose (previously Raftilose®) or 10% inulin such as in the product sold by BENEO-Orafti under the trademark Orafti® inulin (previously Raftiline®). A particularly preferred combination of prebiotics is 70% short chain fructo-oligosaccharides and 30% inulin, which is a product sold by BENEO-Orafti under the trademark "Prebio 1".

The food product of the invention preferably comprises hydrolysed proteins. This is the basis of a synergy effect for the enhancement of oral tolerance to allergens, especially food allergens.

Hydrolysed proteins may be characterised as "partially hydrolysed" or "extensively hydrolysed" depending on the degree to which the hydrolysis reaction is carried out. Currently there is no agreed legal/clinical definition of Extensively Hydrolyzed Products according to the WAO (World Allergy Organization) guidelines for Cow's milk protein allergy (CMA) but there is agreement that according to the WAO that hydrolysed formulas have proven to be a useful and widely used protein source for infants suffering from CMA. In the current invention partially hydrolysed proteins are one in which 60-70% of the protein/peptide population has a molecular weight of less than 1000 Daltons, whereas extensively hydrolysed proteins are one in which at least 95% of the protein/peptide population has a molecular weight of less than 1000 Dalton. These definitions are currently used in the industry. Partially hydrolysed proteins are usually considered as hypoallergenic (HA) whereas extensively hydrolysed proteins are usually considered as non-allergenic. Hydrolyzed proteins and/or partially hydrolyzed proteins can reduce the risk of allergies (to cow milk or other types of allergens).

The food product of the invention can comprise hydrolysed proteins. The hydrolyze proteins can preferably have between 10% and 100%, more preferably between 15% and 95%, of their protein/peptide population having a molecular weight of less than 1000 Dalton.

The hydrolysed proteins of the invention may have an extent of hydrolysis that is characterised by NPN/TN %. Non-Protein Nitrogen over Total Nitrogen is widely use as a measure of soluble peptides created by enzymatic hydrolysis. NPN/TN % means the Non Protein Nitrogen divided by the Total Nitrogen X 100. NPN/TN % may be measured as detailed in Adler-Nissen J-, 1979, J. Agric. Food Chem., 27 (6), 1256-1262. In general, extensively hydrolysed proteins are characterised as having a NPN/TN % of greater than 95%, whereas partially hydrolysed proteins are characterized as having a NPN/TN % in the range 75%-85%. In a preferred embodiment the hydrolysed proteins of the invention have an NPN/TN % in the range of 70-90%, preferably 75 to 85%. The latter hydrolysed proteins are "partially" hydrolysed proteins. These hydrolysed proteins may also be characterised in that 60-70% of their protein/peptide population has a molecular weight of less than 1000 Daltons According to the invention, the extent of hydrolysis of the hydrolysed proteins is within the range of between 50 and 100, preferably between 65 and 99 of NPN/TN %.

In another preferred embodiment where "extensively" hydrolysed proteins are desired the hydrolysed proteins of the invention has a NPN/TN % in the range of greater than 95%. This hydrolysed proteins may also be characterised in that at least 95% of their protein/peptide population has a molecular weight of less than 1000 Daltons.

The extent of hydrolysis can also be measured using a reagent such as trinitrobenzenesulfonic acid (TNBS) which reacts with free lysine. The TNBS reactive Nitrogen % amino (lysine) N/TN of the hydrolysed proteins according to the invention is usually within the range from 8-15%, preferably 9-14%.

According to preferred embodiment of the invention, the food product according to the invention is preferably, for use in preventing and reducing the risk and/or reducing the severity and/or reducing the occurrence of food allergies and related food allergy effects on health. Said effects are preferably (i) skin effects, atopic dermatitis, rash, or redness ; (ii) effects on the immune system or inflammation status ; or (iii) effects on the gastro-intestinal system such as colics, abdominal pain and the like.

According to another embodiment of the invention, the food product according to the invention is for use in the enhancement of the oral tolerance to allergens.

According to a preferred embodiment, the food product according to the invention is for use in infants and young children, preferably it is an infant formula, follow-up formula growing-up milk or baby food.

The invention includes also the use of a food product comprising the oligosaccharide mixture of the invention as a synthetic nutritional composition (i.e. as a synthetic nutritional agent), for preventing and reducing the risk and/or reducing the severity and/or reducing the occurrence of food allergies and related food allergy effects on health.

The invention includes also the use of a food product comprising the oligosaccharide mixture of the invention as a synthetic nutritional composition (i.e. as a synthetic nutritional agent), for the enhancement of the oral tolerance to allergens.

In one embodiment the invention encompasses the use of the mixture of oligosaccharides of the invention, as claimed, for alleviating the occurrence or severity of allergies or inflammation-related conditions. In one embodiment the use is for enhancing the immune status and/or protection against infections. In one embodiment the use is for reducing the abdominal pain and/or alleviating the gut discomfort and/or improving the status of the digestive tract. In one embodiment the population targeted by the invention is a population of infants or children—especially those infants at risk of developing undesired conditions such as allergies, chronic inflammation, skin redness, rash, gut pain or infections. More particularly those having a family history of such conditions or having already experienced some episodes of those conditions are particularly targeted. In one embodiment the composition and uses of the invention apply to teenagers or adults at risk of the above conditions or having experienced episodes of the above conditions (especially respiratory allergies or skin allergies).

These uses encompass the case where the food product mixture is a supplement, preferably provided in the form of unit doses.

The food product may be prepared in any suitable manner known in the art according to the type of product, and the oligosaccharide mixture of the invention may be added to the product at an appropriate stage during the manufacturing process. For example, an infant formula may be prepared by blending together the protein source, together with any carbohydrates other than lactose, and the fat source in appropriate proportions. Emulsifiers may be added if desired. Vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

The homogenised mixture is transferred to a suitable drying apparatus such as a spray dryer or freeze dryer and converted to powder. The powder should have a moisture content of less than about 5% by weight. The N-acetylated-oligosaccharide(s), galacto-oligosaccharide(s), sialylated oligosaccharide(s) and fucosylated oligosaccharide(s) may be added at this stage by dry-mixing along with the probiotic bacterial strain(s) if used, or by blending them in a syrup form of crystals, along with the probiotic bacterial strain(s) if used, and spray-dry (or freeze-dry).

The oligosaccharide mixture of the invention is preferably added directly to infant formula by dry mixing. However, if it has been prepared from an animal milk, for example as described below, it may be convenient to add the oligosaccharide mixture without first removing all the lactose. As an infant formula contains a carbohydrate component which is often wholly or partially constituted by lactose, it will be apparent to the person skilled in the art that the amount of carbohydrate in the infant formula will need to be adjusted to take into account the additional carbohydrate that will be provided by the added oligosaccharide mixture. The final concentration of the oligosaccharide mixture in the young child or infant food product or formula is preferably from 0.3 to 4%, preferably from 0.75 to 1.54% by weight of dry matter. This corresponds to a concentration of from 0.2 to 5 grams per litre of reconstituted formula, preferably from 1 to 2 g/l. However, these amounts should not be construed as limitative and should be adapted to the target population, for example based on the weight and age or health of the young child or infant. Preferably, the formula or feed containing the oligosaccharide mixture of the invention is given to the infant each time it is fed.

Alternatively, the oligosaccharide mixtures may be added to wet infant or adult food products by wet mixing. The mixture may be added to the infant formula at concentrations of from about 0.2 to about 5 grams of oligosaccharides per litre of product. However, these amounts should not be construed as limitative and should be adapted to the target population, for example based on the weight and age of the young child or infant, or the health of the specific population. When wet mixing is used, the oligosaccharide blend is preferably added in the form of syrup. The syrup may contain up to 80% total solids, but this should not be limitative.

Although it is preferred to supplement food products specifically targeted towards infant nutrition, it may be beneficial to supplement food products, which are not specifically targeted, or are targeted at the adult population. For example, the oligosaccharide mixtures of the invention can be incorporated into healthcare nutrition products and nutritional products for the elderly. Such food products may include milk, yoghurt, curd, cheese, ice cream, among others. Such food products include also oral food supplement, and enteral nutrition preparations or example for tube feeding administration.

The invention will now be illustrated by reference to the following examples.

EXAMPLE 1

One method of preparing an oligosaccharide mixture according to the invention will now be described by way of example only.

200,000 litres of a whey ultrafiltration permeate are pre-concentrated to 22% (w/w) total solids (TS), pasteurised at about 75° C. for about 30 seconds and then concentrated by evaporation at 60° C. to reach a TS of 59% (w/w . The liquid is cooled in a crystalliser at a rate of 2° C. per hour for a period of 24 hours to crystallise the lactose. Crystallised lactose is washed and than removed using a wringer. The remaining liquid (mother liquor) is clarified by passing it through a decanter. The 77000 litres at 17.7% TS obtained from the clarifier are re-concentrated by evaporation at 60° C. to reach a TS of 55% (w/w), and are then subjected to a second lactose crystallisation step under the same conditions as those described above. The 29000 litres at 20.55 TS of the mother liquor thereby obtained are demineralised by a combination of electrodialysis and ion exchange in a manner known per se, yielding 28500 litres of a 90% demineralised liquor at 17.3% TS. This liquor, which contains approximately 1.5 grams per litre of a mixture of about 30 wt % GalNAα1,3Galβ1,4Glc and Galβ1,6GalNAcα1,3Galβ1,4Glc, 50 wt % of Galβ1, 6Galβ1,6Glc. Galβ1,6Galβ1,4Glc and Galβ1,3Galβ1,4Glc and 20 wt % of NeuAcα2,3Galβ1,4Glc and NeuAcα2, 6Galβ1,4Glc, depending upon the starting material, may either be added directly to a food product such as an infant formula or may by further concentrated in a manner known to those skilled in the art.

For example, the lactose remaining in the liquor may be hydrolysed into glucose and galactose and these monosaccharides may either be removed by nanofiltration or, if desired, the galactose may be at least partially polymerised for example by the action of β-galactosidase to produce galacto-oligosaccharides which will also be retained by the nanofiltration membrane.

Fucα1,2Galβ1,4Glc (2'-fucosyllactose), which is commercially available from Kyowa Hakko Kogyo of Japan, may be directly added to the food product at the same time as the liquor directly to the food product. Preferably, it is mixed with the liquor concentrate and the mixture is further added to the food product.

EXAMPLE 2

An example of an infant formula containing an oligosaccharide according to the present invention is given below. Another example (example 3) is based on commercial NAN and/or Lactogen Infant formulae (from Nestlé, Switzerland) to which the specific oligosaccharides of the invention are added as in the amount stated below.

| Nutrient | per 100 kcal | per liter |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Oligosaccharide mixture from Example 1 (g) | 0.15 | 1.0 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |

The invention claimed is:

1. A food product comprising: hydrolyzed proteins; and an oligosaccharide mixture which comprises:
   5-70 wt % of at least one N-acetylated oligosaccharide selected from the group consisting of N-acetyl-galactosaminyl-lactose and galactosyl-N-acetyl-galactosaminyl-lactose,
   5-90 wt % of at least one galacto-oligosaccharide selected from the group consisting of Galβ1,6Gal, Galβ1, 6Galβ1,4Glc, Galβ1,6Galβ1,6Glc, Galβ1,3Galβ1, 3Glc, Galβ1,3Galβ1,4Glc, Galβ1,6Galβ1,6Galβ1, 4Glc, Galβ1,6Galβ1,3Galβ1,4Glc, Galβ1,3Galβ1, 6Galβ1,4Glc, Galβ1,3Galβ1,3Galβ1,4Glc, Galβ1,4Galβ1,4Glc and Galβ1,4Galβ1,4Galβ1,4Glc,
2-50 wt % of at least one sialylated oligosaccharide selected from the group consisting of 3'-sialyllactose and 6'-sialyllactose; and
2-70 wt % of at least one fucosylated oligosaccharide selected from the group consisting of 2'-fucosyllactose, 3-fucosyllactose, difucosyllactose, lacto-N-fucopentaoses, lacto-N-difucohexaose I, monofucosyllacto-N-hexaose, Difucosyllacto-N-hexaose I and Difucosyllacto-N-neohexaose II.

2. A food product according to claim 1 comprising a protein source, a fat source, and a carbohydrate source, wherein the protein source comprises the hydrolyzed proteins.

3. The food product according to claim 1, which is selected from the group consisting of a starter infant formula, an infant formula, a baby food, an infant cereal composition, a follow-up formula and a growing-up milk.

4. The food product according to claim 1, wherein the extent of hydrolysis of the hydrolysed proteins is between 50 and 100 of NPN/TN %.

5. The food product according to claim 1, wherein a trinitrobenzenesulfonic acid reactive Nitrogen % that reacts with amino (lysine) N/TN of the hydrolysed proteins is from 8-15%.

6. A method for preventing and reducing the risk of food allergies and related food allergy effects on health of an individual, the method comprising:
administering to the individual oligosaccharide mixture which comprises 5-70 wt % of at least one N-acetylated oligosaccharide selected from the group consisting of N-acetyl-galactosaminyl-lactose and galactosyl-N-acetyl-galactosaminyl-lactose, 5-90 wt % of at least one galacto-oligosaccharide selected from the group consisting of Galβ1,6Gal, Galβ1,6Galβ1,4Glc, Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc, Galβ1,3Galβ1,6Galβ1,4Glc, Galβ1,3Galβ1,3Galβ1,4Glc, Galβ1,4Galβ1,4Glc and Galβ1,4Galβ1,4Galβ1,4Glc, 2-50 wt % of at least one sialylated oligosaccharide selected from the group consisting of 3'-sialyllactose and 6'-sialyllactose; and 2-70 wt % of at least one fucosylated oligosaccharide selected from the group consisting of 2'-fucosyllactose, 3-fucosyllactose, difucosyllactose, lacto-N-fucopentaoses, lacto-N-difucohexaose I, monofucosyllacto-N-hexaose, Difucosyllacto-N-hexaose I and Difucosyllacto-N-neohexaose II.

7. The method according to claim 6, wherein the effects are selected from the group consisting of (i) skin effects, atopic dermatitis, rash, or redness; (ii) effects on the immune system or inflammation status; or (iii) effects on the gastro-intestinal system.

8. The method according to claim 6, wherein the composition provides enhancement of the oral tolerance to allergens.

9. The food product according to claim 1, wherein the food product comprises at least one probiotic bacterial strain.

10. A method for reducing the severity and reducing the occurrence of food allergies and related food allergy effects on health, the method comprising:
administering to an individual an oligosaccharide mixture comprising 5-70 wt % of at least one N-acetylated oligosaccharide selected from the group consisting of N-acetyl-galactosaminyl-lactose and galactosyl-N-acetyl-galactosaminyl-lactose, 5-90 wt % of at least one galacto-oligosaccharide selected from the group consisting of Galβ1,6Gal, Galβ1,6Galβ1,4Glc, Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc, Galβ1,3Galβ1,6Galβ1,4Glc, Galβ1,3Galβ1,3Galβ1,4Glc, Galβ1,4Galβ1,4Glc and Galβ1,4Galβ1,4Galβ1,4Glc, 2-50 wt % of at least one sialylated oligosaccharide selected from the group consisting of 3'-sialyllactose and 6'-sialyllactose, and/or 5-70 wt % of at least one fucosylated oligosaccharide selected from the group consisting of 2'-fucosyllactose, 3-fucosullactose, difucosyllactose, lacto-N-fucopentaoses, lacto-N-difucohexaose I, monofucosyllacto-N-hexaose, Difucosyllacto-N-hexaose I and Difucosyllacto-N-neohexaose II, as a synthetic nutritional composition.

11. A method for the enhancement of oral tolerance to allergens, the method comprising:
administering to an individual a food product comprising 5-70 wt % of at least one N-acetylated oligosaccharide selected from the group consisting of N-acetyl-galactosaminyl-lactose and galactosyl-N-acetyl-galactosaminyl-lactose, 5-90 wt % of at least one galacto-oligosaccharide selected from the group consisting of Galβ1,6Gal, Galβ1,6Galβ1,4Glc, Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc, Galβ1,3Galβ1,6Galβ1,4Glc, Galβ1,3Galβ1,3Galβ1,4Glc, Galβ1,4Galβ1,4Glc and Galβ1,4Galβ1,4Galβ1,4Glc, 2-50 wt % of at least one sialylated oligosaccharide selected from the group consisting of 3'-sialyllactose and 6'-sialyllactose, and/or 5-70 wt % of at least one fucosylated oligosaccharide selected from the group comprising consisting of 2'-fucosyllactose, 3-fucosyllactose, difucosyllactose, lacto-N-fucopentaoses, lacto-N-difucohexaose I, monofucosyllacto-N-hexaose, Difucosyllacto-N-hexaose I and Difucosyllacto-N-neohexaose II, as a synthetic nutritional composition.

12. The method according to claims 10, wherein the food product is a supplement.

13. The method according to claim 10 wherein the food product comprises fully hydrolyzed and/or partially hydrolyzed proteins.

14. The method according to claim 11, wherein the food product is a supplement.

15. The method according to claim 11 wherein the food product comprises fully hydrolyzed and/or partially hydrolyzed proteins.

* * * * *